United States Patent [19]

Maubru et al.

[11] Patent Number: 5,785,717
[45] Date of Patent: Jul. 28, 1998

[54] COMPOSITION FOR THE OXIDATION DYEING OF KERATIN FIBERS, COMPRISING A DIAMINOPYRAZOLE DERIVATIVE AND A HETEROCYCLIC COUPLER, AND DYEING PROCESS

[75] Inventors: Mireille Maubru, Chatou; Marie-Pascale Audousset, Asnieres, both of France

[73] Assignee: L'Oreal, Paris, France

[21] Appl. No.: 606,749

[22] Filed: Feb. 27, 1996

[30] Foreign Application Priority Data

Feb. 27, 1995 [FR] France .................... 95 02271

[51] Int. Cl.⁶ ........................................ A61K 7/13
[52] U.S. Cl. .................... 8/409; 8/408; 8/423; 8/565; 8/568; 8/569; 8/573; 8/574; 8/576
[58] Field of Search ................ 8/406, 408, 423, 8/409, 565, 568, 569, 573, 574, 576

[56] References Cited

U.S. PATENT DOCUMENTS

| | | | |
|---|---|---|---|
| 3,200,040 | 8/1965 | Lange | 8/409 |
| 3,649,160 | 3/1972 | Kalopissis et al. | 8/10.2 |
| 3,658,455 | 4/1972 | Kalopissis et al. | 8/409 |
| 3,690,810 | 9/1972 | Bugaut et al. | 8/409 |
| 4,402,698 | 9/1983 | Kalopissis et al. | 8/406 |
| 4,692,166 | 9/1987 | Junino et al. | 8/410 |
| 5,061,289 | 10/1991 | Clausen et al. | 8/405 |
| 5,131,911 | 7/1992 | Lang et al. | 8/405 |
| 5,207,798 | 5/1993 | Cotteret et al. | 8/408 |
| 5,279,620 | 1/1994 | Junino et al. | 8/423 |
| 5,354,870 | 10/1994 | Lang et al. | 548/469 |
| 5,364,414 | 11/1994 | Lang et al. | 8/423 |
| 5,380,340 | 1/1995 | Neunhoeffer et al. | 8/409 |
| 5,391,206 | 2/1995 | Cotteret | 8/408 |
| 5,451,236 | 9/1995 | Junino et al. | 8/408 |
| 5,478,359 | 12/1995 | LaGrange et al. | 8/412 |
| 5,505,741 | 4/1996 | Junino et al. | 8/408 |
| 5,518,505 | 5/1996 | Cotteret et al. | 8/409 |
| 5,518,506 | 5/1996 | Cotteret et al. | 8/409 |
| 5,534,036 | 7/1996 | Junino et al. | 8/411 |
| 5,534,267 | 7/1996 | Neunhoeffer et al. | 424/701 |

FOREIGN PATENT DOCUMENTS

| | | |
|---|---|---|
| A-0375977 | 7/1990 | European Pat. Off. |
| A-0428441 | 5/1991 | European Pat. Off. |
| A-0446132 | 9/1991 | European Pat. Off. |
| A-0465339 | 1/1992 | European Pat. Off. |
| A-0465340 | 1/1992 | European Pat. Off. |
| A-0634164 | 1/1995 | European Pat. Off. |
| A-1916139 | 11/1969 | Germany . |
| A-3031709 | 4/1982 | Germany . |
| A-3743769 | 7/1989 | Germany . |
| A-3930446 | 3/1990 | Germany . |
| A-4133957 | 4/1993 | Germany . |
| A-1217479 | 12/1970 | United Kingdom . |
| A-2180215 | 3/1987 | United Kingdom . |
| WO-A-9309759 | 5/1993 | WIPO . |
| WO-A-9408970 | 4/1994 | WIPO . |

OTHER PUBLICATIONS

English Derwent Abstract of DE-A-3743769, Jul. 1989.
English Derwent Abstract of DE-A-3031709, Apr. 1982.
English Derwent Abstract of EP-A-0634164, Jan. 1995.
English Derwent Abstract of EP-A-0428441, May 1991.
English Derwent Abstract of EP-A-0465339, Jan. 1992.
English Derwent Abstract of WO-A-9408970, Apr. 1994.
ASTM Designation:D 1535-95b, "Standard Practice for Specifying Color by the Munsell System," pp. 1–3, No date available.

*Primary Examiner*—Paul Lieberman
*Assistant Examiner*—Caroline L. Duscheck
*Attorney, Agent, or Firm*—Finnegan, Henderson, Farabow, Garrett & Dunner, L.L.P.

[57] ABSTRACT

The present invention relates to a composition for the oxidation dyeing of keratin fibers, in particular human keratin fibers such as the hair, comprising at least one diaminopyrazole derivative as oxidation base in combination with at least one suitably selected heterocyclic coupler, and to the dyeing process using this composition with an oxidizing agent.

24 Claims, No Drawings

COMPOSITION FOR THE OXIDATION DYEING OF KERATIN FIBERS, COMPRISING A DIAMINOPYRAZOLE DERIVATIVE AND A HETEROCYCLIC COUPLER, AND DYEING PROCESS

The present invention relates to a composition for the oxidation dyeing of keratin fibers, in particular human keratin fibers such as the hair, comprising at least one diaminopyrazole derivative as oxidation base in combination with at least one suitably selected heterocyclic coupler, and to the dyeing process using this composition with an oxidizing agent.

It is known to dye keratin fibers, and in particular human hair, with dye compositions containing oxidation dye precursors, in particular ortho- or para-phenylenediamines, ortho- or para-aminophenols and heterocyclic compounds such as diaminopyrazole derivatives, which are generally referred to as oxidation bases. The oxidation dye precursors, or oxidation bases, are colorless or weakly colored compounds which, when combined with oxidizing products, may give rise to colored compounds and dyes by a process of oxidative condensation.

It is also known that the shades obtained with these oxidation bases may be varied by combining them with couplers or coloration modifiers, the latter being chosen in particular from aromatic meta-diamines, meta-aminophenols, meta-diphenols and certain heterocyclic compounds such as indole derivatives and, in particular, 4-hydroxyindole.

The variety of molecules used as oxidation bases and couplers makes it possible to obtain a wide range of colors.

The so-called "permanent" coloration obtained by means of these oxidation dyes should highly preferably, moreover, satisfy a certain number of requirements. Thus, it should highly preferably have no toxicological drawbacks, should highly preferably allow shades of the desired strength to be obtained and should highyl preferably have good resistance to external agents (light, inclement weather, washing, permanent-waving, perspiration and friction).

The dyes should highly preferably also allow white hairs to be covered and, lastly, they should highly preferably be as unselective as possible, that is to say that they should highly preferably allow the smallest possible differences in coloration to be produced over the entire length of the same keratin fiber, which may indeed be differently sensitized (i.e., damaged) between its tip and its root.

Compositions for the oxidation dyeing of keratin fibers comprising a diaminopyrazole derivative as oxidation base, in combination with a coupler which may be chosen from various types of couplers such as resorcin, 4-chlororesorcin, meta-aminophenols, meta-phenylenediamines, α-naphthol, couplers of heterocyclic type such as 4-hydroxyindole, 4-hydroxy-1,2-methylenedioxybenzene, 3-amino-5-hydroxy-2,6-dimethoxypyridine or 3,5-diamino-2,6-dimethoxypyridine and the like, have already been proposed, in particular in German patent applications DE 3,843,892 and 4,133,957. However, such compositions are not entirely satisfactory, especially from the point of view of their tenacity, and in particular from the point of view of the fastness of the colorations obtained with respect to perspiration.

The inventors have discovered that it is possible to obtain novel dyes which are quite unselective and particularly resistant, especially to perspiration, and which are capable of giving rise to strong colorations, by combining at least one diaminopyrazole derivative of formula (I) defined below and at least one suitably selected heterocyclic coupler.

This discovery forms the basis of the present invention.

The subject of the invention is thus a composition for the oxidation dyeing of keratin fibers, and in particular human keratin fibers such as the hair, characterized in that it comprises, in a medium which is suitable for dyeing:

at least one oxidation base chosen from the diaminopyrazole derivatives of following formula (I), and the acid addition salts thereof:

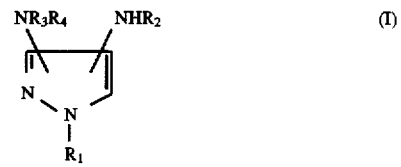

in which:

$R_1$ represents a hydrogen atom, a $C_1$–$C_6$ alkyl, $C_2$–$C_4$ hydroxyalkyl, benzyl or phenyl radical, a benzyl radical substituted with a halogen atom or with a $C_1$–$C_4$ alkyl or $C_1$–$C_4$ alkoxy group, or forms, with the nitrogen atom of either $NR_3R_4$ or $NHR_2$ substituted at the 5-position, a hexahydropyrimidine or tetrahydroimidazole heterocycle optionally monosubstituted with a $C_1$–$C_4$ alkyl group;

$R_2$ and $R_3$, which may be identical or different, represent a hydrogen atom or a $C_1$–$C_4$ alkyl, $C_2$–$C_4$ hydroxyalkyl, benzyl or phenyl radical;

$R_4$ represents a hydrogen atom or a $C_1$–$C_6$ alkyl or $C_2$–$C_4$ hydroxyalkyl radical;

with the proviso that $R_2$ represents a hydrogen atom when $R_1$ represents a substituted benzyl radical, or forms a heterocycle with the nitrogen atom in the 5-position:

at least one heterocyclic coupler chosen from:

(i) indole derivatives of following formula (II), and the acid addition salts thereof:

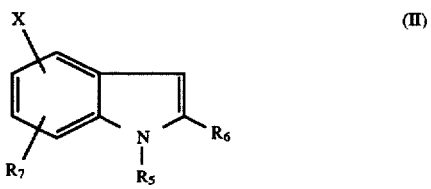

in which:

$R_5$ and $R_6$, which may be identical or different, represent a hydrogen atom or a $C_1$–$C_4$ alkyl radical;

$R_7$ represents a hydrogen atom or a $C_1$–$C_4$ alkyl or hydroxyl radical;

X represents a hydroxyl radical or a radical $NHR_8$ in which $R_8$ represents a hydrogen atom or a $C_1$–$C_4$ alkyl or $C_1$–$C_4$ hydroxyalkyl radical;

with the proviso that:
when $R_7$ denotes hydroxyl, it then occupies the 6-position and X then denotes hydroxyl and occupies the 5-position and $R_5$ and $R_6$ represent a hydrogen atom, when X denotes hydroxyl and occupies the 4-position, then at least one of the radicals $R_5$, $R_6$ and $R_7$ is other than a hydrogen atom, when X is in the 5-position, then at least one of the radicals $R_5$, $R_6$ and $R_7$ is other than a hydrogen atom;

(ii) the benzimidazole derivatives of following formula (III), and the acid addition salts thereof:

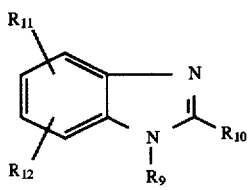

(III)

in which:

$R_9$ represents a hydrogen atom or a $C_1$–$C_4$ alkyl radical.

$R_{10}$ represents a hydrogen atom or a $C_1$–$C_4$ alkyl or phenyl radical.

$R_{11}$ represents a hydroxyl, amino or methoxy radical, $R_{12}$ represents a hydrogen atom or a hydroxyl, methoxy or $C_1$–$C_4$ alkyl radical;

with the proviso that:
when $R_{11}$ denotes an amino radical, it then occupies the 4-position,
when $R_{11}$ occupies the 4-position, $R_{12}$ then occupies the 7-position,
when $R_{11}$ occupies the 5-position, $R_{12}$ then occupies the 6-position;

(iii) the benzomorpholine derivatives of following formula (IV), and the acid addition salts thereof:

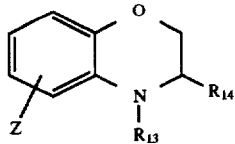

(IV)

in which:

$R_{13}$ and $R_{14}$, which may be identical or different, represent a hydrogen atom or a $C_1$–$C_4$ alkyl radical, Z represents a hydroxyl or amino radical;

(iv) the pyridine derivatives of following formula (V), and the acid addition salts thereof:

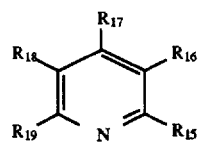

(V)

in which:

$R_{15}$ represents a hydrogen atom or a hydroxyl, amino or —$OCH_2CH_2COCH_2CH_2OH$ radical, $R_{16}$ and $R_{18}$, which may be identical or different, represent a hydrogen atom or a hydroxyl, amino or $C_1$–$C_4$ alkyl radical, $R_{17}$ represents a hydrogen atom or a $C_1$–$C_4$ alkyl radical, $R_{19}$ represents a hydrogen atom or a hydroxyl or amino radical, it being understood that these compounds of formula (V) do not contain more than two amino groups (substituted or unsubstituted) or not more than two hydroxyl groups or not more than one amino group and one hydroxyl group per molecule, these amino and/or hydroxyl groups necessarily being in a meta position relative to each other;

(v) indoline derivatives of following formula (VI), and the acid addition salts thereof:

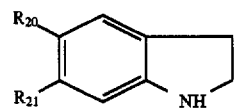

(VI)

in which:

$R_{20}$ denotes a hydrogen atom or a hydroxyl radical, $R_{21}$ denotes a hydroxyl or amino radical;

(vi) the quinoline derivatives of following formula (VII), and the acid addition salts thereof:

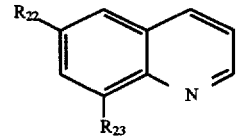

(VII)

in which:

$R_{22}$ denotes a hydroxyl or $C_1$–$C_4$ alkoxy radical, $R_{23}$ denotes a hydrogen atom or amino radical;

(vii) the sesamol derivatives of following formula (VIII), and the acid addition salts thereof:

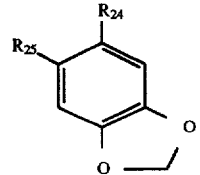

(VIII)

in which:

$R_{24}$ denotes a hydroxyl or amino radical, $R_{25}$ denotes a halogen atom or a $C_1$–$C_4$ alkoxy radical, with the proviso that:
when $R_{24}$ denotes an amino radical, $R_{25}$ then denotes a $C_1$–$C_4$ alkoxy radical,
when $R_{24}$ denotes a hydroxyl radical, $R_{25}$ then denotes a halogen atom;

it being understood that when the said composition comprises a compound of formula (I) which is 4,5-diamino-1-methylpyrazole, it then does not contain any indole derivative of formula (II) which is 5,6-dihydroxyindole.

The colorations obtained with the oxidation dye composition in accordance with the invention have good dyeing power and excellent properties of resistance both to atmospheric agents such as light and inclement weather and to perspiration and the various treatments to which the hair may be subjected (shampooing, permanent waving). These properties are particularly noteworthy, especially with respect to the resistance of the colorations obtained to perspiration.

The subject of the invention is also a process for the oxidation dyeing of keratin fibers using this composition.

The acid addition salts which may be used in the context of the dye compositions of the invention are chosen in particular from the hydrochlorides, hydrobromides, sulphates and tartrates.

Among the diaminopyrazole derivatives of above formula (I) which may be mentioned more particularly are 4,5-diamino-1-(4'-methoxybenzyl)pyrazole, 4,5-diamino-1-(4'-methylbenzyl)pyrazole, 4,5-diamino-1-(4'-chlorobenzyl)pyrazole, 4,5-diamino-1-(3'-methoxybenzyl)pyrazole, 4-amino-1-(4'-methoxybenzyl)-5-methylaminopyrazole, 4-amino-5-(β-hydroxyethyl)amino-1-(4'-methoxybenzyl)pyrazole, 4-amino-5-(β-hydroxyethyl)amino-1-methylpyrazole, 4-amino-(3) 5-methylaminopyrazole, 3(5), 4-diaminopyrazole, 4,5-diamino-1-methylpyrazole, 4,5-diamino-1-benzylpyrazole, 3-amino-4,5,7,8-tetrahydropyrazolo[1,5-a]pyrimidine, 7-amino-2,3-dihydro-1H-imidazo[1,2-b]pyrazole and 3-amino-8-methyl-4,5,7,8-tetrahydropyrazolo[1,5-a]pyrimidine, and the acid addition salts thereof.

Among the indole derivatives of above formula (II) which may be mentioned more particularly are 6-hydroxyindole, 7-aminoindole, 6-aminoindole, 7-hydroxyindole, 7-ethyl-6-(β-hydroxyethyl)aminoindole, 4-aminoindole, 6-hydroxy-1-methylindole, 5,6-dihydroxyindole, 4-hydroxy-1-N-methylindole, 4-hydroxy-2-methylindole and 4-hydroxy-5-methylindole, and the acid addition salts thereof.

Among the benzimidazole derivatives of above formula (III) which may be mentioned more particularly are 4-hydroxybenzimidazole, 4-aminobenzimidazole, 4-hydroxy-7-methylbenzimidazole, 4-hydroxy-2-methylbenzimidazole, 1-butyl-4-hydroxybenzimidazole, 4-amino-2-methylbenzimidazole, 5,6-dihydroxybenzimidazole, 5-hydroxy-6-methoxybenzimidazole, 4,7-dihydroxybenzimidazole, 4,7-dihydroxy-1-methylbenzimidazole, 4,7-dimethoxybenzimidazole, 5,6-dihydroxy-1-methylbenzimidazole, 5,6-dihydroxy-2-methylbenzimidazole and 5,6-dimethoxybenzimidazole, and the acid addition salts thereof.

Among the benzomorpholine derivatives of above formula (IV) which may be mentioned more particularly are 6-hydroxy-benzomorpholine, N-methyl-6-hydroxy-benzomorpholine and 6-amino-benzomorpholine, and the acid addition salts thereof.

Among the pyridine derivatives of above formula (V) which may be mentioned more particularly are 2,6-dihydroxy-4-methylpyridine, 2,6-dihydroxy-3,4-dimethylpyridine, 2,6-diaminopyridine, 3-oxo-5-(3',5'-diamino-2'-pyridyloxy)pentanol and 3-(3',5'-diamino-2'-pyridyloxy)-2-hydroxypropanol, and the acid addition salts thereof.

Among the indoline derivatives of above formula (VI) which may be mentioned are 6-hydroxyindoline, 6-aminoindoline and 5,6-dihydroxyindoline, and the acid addition salts thereof.

Among the quinoline derivatives of above formula (VII) which may be mentioned more particularly are 6-hydroxyquinoline and 8-amino-6-methoxyquinoline, and the acid addition salts thereof.

Among the sesamol derivatives of above formula (VIII) which may be mentioned more particularly are 2-bromo-4,5-methylenedioxyphenol and 2-methoxy-4,5-methylenedioxyphenylene, and the acid addition salts thereof.

The diaminopyrazole derivative or derivatives of formula (I) in accordance with the invention preferably represent approximately from 0.0005 to 12% by weight relative to the total weight of the dye composition, and even more preferably approximately from 0.005 to 6% by weight relative to this weight.

The heterocyclic coupler or couplers in accordance with the invention preferably represent approximately from 0.0001 to 10% by weight relative to the total weight of the dye composition, and even more preferably approximately from 0.005 to 5% by weight relative to this weight.

The appropriate medium for the dyeing (or the support) generally consists of water or of a mixture of water and at least one organic solvent to solubilize the compounds which would not be sufficiently soluble in water. Organic solvents which may be mentioned, for example, are $C_1$–$C_4$ lower alkanols such as ethanol and isopropanol; glycerol; glycols and glycol ethers such as 2-butoxyethanol, propylene glycol, propylene glycol monomethyl ether, diethylene glycol monomethyl ether and monoethyl ether, as well as aromatic alcohols such as benzyl alcohol or phenoxyethanol, similar products and mixtures thereof.

The solvents may be present in proportions preferably of approximately from 1 to 40% by weight relative to the total weight of the dye composition, and even more preferably of approximately from 5 to 30% by weight.

The pH of the dye composition in accordance with the invention is generally from 3 to 12. It may be adjusted to the desired value using acidifying or basifying agents usually used in the dyeing of keratin fibers.

Among the acidifying agents which may be mentioned, by way of example, are inorganic or organic acids such as hydrochloric acid, orthophosphoric acid, carboxylic acids such as tartaric acid, citric acid and lactic acid, and sulfonic acids.

Among the basifying agents which may be mentioned, by way of example, are aqueous ammonia, alkaline carbonates, alkanolamines such as mono-, di- and triethanolamines and derivatives thereof, sodium hydroxide, potassium hydroxide and the compounds of following formula (IX):

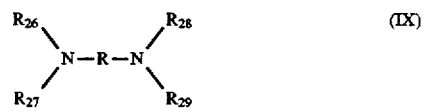

in which R is a propylene residue optionally substituted with a hydroxyl group or a $C_1$–$C_4$ alkyl radical; $R_{26}$, $R_{27}$, $R_{28}$ and $R_{29}$, which may be identical or different, represent a hydrogen atom or a $C_1$–$C_4$ alkyl or $C_1$–$C_4$ hydroxyalkyl radical.

In addition to the dyes defined above, the dye composition in accordance with the invention may also contain other oxidation bases and/or other couplers and/or direct dyes, in particular in order to modify the shades or to enrich them with glints.

The dye composition according to the invention may also include various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifying agents.

Obviously, a person skilled in the art will take care to choose this or these optional complementary compound(s) such that the advantageous properties intrinsically associated with the binary combination in accordance with the invention are not, or are substantially not, adversely affected by the addition or additions envisaged.

The dye composition according to the invention may be in various forms, such as in the form of liquids, creams, gels or any other form which is suitable for dyeing keratin fibers, and in particular human hair.

The subject of the invention is also a process for dyeing keratin fibers, and in particular human keratin fibers such as the hair, using the dye composition as defined above.

According to this process, the dye composition as defined above is applied to the fibers, the color being developed at acidic, neutral or alkaline pH using an oxidizing agent which is added only at the time of use to the dye composition or which is present in an oxidizing composition that is applied simultaneously or sequentially in a separate manner, i.e., the oxidizing composition is applied from a separate dispenser than the dye composition, either at the same time (simultaneously) as the dye composition or sequentially with it.

According to a particularly preferred embodiment of the dyeing process according to the invention, the dye composition described above is mixed, at the time of use, with an oxidizing composition containing, in a medium which is suitable for dyeing, at least one oxidizing agent present in an amount which is sufficient to develop a coloration. The mixture obtained is then applied to the keratin fibers and is left in place for 3 to 50 minutes approximately, preferably 5 to 30 minutes approximately, after which the fibers are rinsed, washed with shampoo, rinsed again and dried.

The oxidizing agent present in the oxidizing composition as defined above may be chosen from the oxidizing agents conventionally used for the oxidation dyeing of keratin fibers, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resulting composition applied to the keratin fibers preferably varies approximately from 3 to 12 and even more preferably from 5 to 11. It is adjusted to the desired value using acidifying or basifying agents usually used in the dyeing of keratin fibers and as are defined above.

The oxidizing composition as defined above may also include various adjuvants used conventionally in compositions for dyeing the hair and as are defined above.

The composition which is finally applied to the keratin fibers may be in various forms, such as in the form of liquids, creams, gels or any other form which is suitable for dyeing keratin fibers, and in particular human hair.

Another subject of the invention is a multi-compartment device or dyeing kit or any other multi-compartment packaging system, a first compartment of which contains the dye composition as defined above and a second compartment of which contains the oxidizing composition as defined above. These devices may be equipped with a means which makes it possible to deliver the desired mixture onto the hair, such as the devices described in patent FR-2,586,913, assigned to the same assignee as the present application.

The examples which follow are intended to illustrate the invention without, however, limiting the scope thereof.

EXAMPLES

The following dye compositions A-F were prepared (contents in grams):

| COMPOSITION | A(*) | B | C | D | E | F |
|---|---|---|---|---|---|---|
| 4,5-Diaminopyrazole dihydrochloride | 0.513 | 0.513 | 0.513 | 0.513 | 0.513 | 0.513 |
| 4-Hydroxyindole | 0.399 | | | | | |
| 4-Hydroxy-1-N-methylindole | | 0.442 | | | | |
| 7-Aminoindole hydrobromide | | | 0.639 | | | |
| 6-Hydroxyindole | | | | 0.399 | | |
| 4-Hydroxybenzimidazole hydrobromide | | | | | 0.645 | |
| 6-Hydroxyindoline hydrochloride | | | | | | 0.515 |
| Common dye support () | () | () | () | () | () | (**) |
| demineralized water q.s. | 100 g | 100 g | 100 g | 100 g | 100 g | 100 g |

| COMPOSITION | A(*) | B | C | D | E | F |
|---|---|---|---|---|---|---|

(*): Dye composition not forming part of the invention
(**): Common dye support:

| | |
|---|---|
| Oleyl alcohol polyglycerolated with 2 mol of glycerol | 4.0 g |
| Oleyl alcohol polyglycerolated with 4 mol of glycerol, containing 78% of active material (AM) | 5.69 g AM |
| Oleic acid | 3.0 g |
| Oleylamine containing 2 mol of ethylene oxide, sold under the trade name Ethomeen O12 by the company AKZO | 7.0 g |
| Diethylaminopropyl laurylaminosuccinamate, sodium salt, containing 55% of AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution, containing 35% of AM | 0.455 g AM |
| Ammonium acetate | 0.8 g |
| Antioxidant, sequestering agent | qs |
| Fragrance, preserving agent | qs |
| Aqueous ammonia containing 20% of $NH_3$ | 10.0 g |

Each dye composition was mixed, at the time of use, with an equal weight amount of an oxidizing composition consisting of 20-volumes aqueous hydrogen peroxide solution (6% by weight).

Each mixture obtained was applied for 30 minutes to locks of permanent-waved grey hair containing 90% white hairs. The locks of hair were then rinsed, washed with a standard shampoo and then dried.

The color of the locks was then evaluated in the Munsell system using a Minolta CM 2002 colorimeter.

The locks of hair thus treated were then subjected to a perspiration resistance test. To do this, the locks of hair were immersed in a crystallizing dish covered with a watch glass and containing a synthetic sweat solution of the following composition:

| | |
|---|---|
| NaCl | 1 g |
| Potassium hydrogen phosphate | 0.1 g |
| Histidine | 0.025 g |
| Lactic acid qs | pH 3.2 |
| Distilled water qs | 100 g |

The locks of dyed hair were left to stand in this synthetic sweat solution for 48 hours at 37° C. The locks were then rinsed and dried.

The color of the locks was then re-evaluated in the Munsell system using a Minolta CM 2002 colorimeter so as to determine the degradation of the colorations after this perspiration resistance test.

According to the Munsell notation, a color is defined by the expression HV/C in which the three parameters respectively denote the shade or Hue (H), the intensity or Value (V) and the purity or Chromaticity (C), the oblique line in this expression simply being a convention and not indicating a ratio.

The difference in color between two locks (here, before and after the treatment simulating perspiration) is calculated by applying the Nickerson formula: $\Delta E = 0.4 C_o \Delta H + 6 \Delta V + 3 \Delta C$, as described, for example, in "Couleur, Industrie et Technique"; pages 14–17; vol. No. 5; 1978. In this formula, ΔE represents the difference in color between two locks, ΔH, ΔV and ΔC represent the variation in absolute value of the parameters H, V and C, and $C_o$ represents the purity of the lock relative to which it is desired to evaluate the color difference.

The results are given in the table below:

| COMPO-SITION | Color of the hair before the test | Color of the hair after the test | Degradation of the color | | | |
|---|---|---|---|---|---|---|
| | | | ΔH | ΔV | ΔC | ΔE |
| A(*) | 6.9 RP 2.8/6.3 | 8/8 RP 2.9/3.4 | 1.9 | 0.1 | 2.9 | 14.1 |
| B | 6.1 RP 3.1/6.1 | 8.3 RP 3.4/5.2 | 2.2 | 0.3 | 0.9 | 9.9 |
| C | 1.1 B 3.4/0.2 | 9.0 YR 3.9/1.4 | 42.2 | 0.5 | 1.2 | 10.0 |
| D | 4.3 YR 4.4/3.9 | 7.3 YR 4.8/2.9 | 3.0 | 0.4 | 1.0 | 10.1 |
| E | 8.4 RP 2.8/6.8 | 8.3 RP 3.3/5.1 | 0.1 | 0.5 | 1.7 | 8.4 |
| F | 8.0 R 3.6/1.2 | 2.3 YR 3.5/1.6 | 4.3 | 0.1 | 0.4 | 3.9 |

(*): Composition not forming part of the invention

These results show that the compositions B to F in accordance with the invention lead to a coloration which is much more resistant to perspiration than the composition A not forming part of the invention.

What is claimed is:

1. A composition for the oxidation dyeing of keratin fibers, said composition comprising, in a medium which is suitable for dyeing:

at least one oxidation base selected from the diaminopyrazole derivatives of following formula (I), and the acid addition salts thereof:

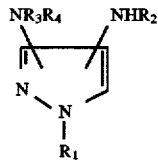

in which:

$R_1$ represents a hydrogen atom, a $C_1$–$C_6$ alkyl, $C_2$–$C_4$ hydroxyalkyl, benzyl or phenyl radical, a benzyl radical substituted with a halogen atom or with a $C_1$–$C_4$ alkyl or $C_1$–$C_4$ alkoxy group, or forms, with the nitrogen atom of $NR_3R_4$ in the 5-position, a hexahydropyrimidine or tetrahydroimidazole heterocycle optionally monosubstituted with a $C_1$–$C_4$ alkyl group;

$R_2$ and $R_3$, which may be identical or different, represent a hydrogen atom or a $C_1$–$C_4$ alkyl, $C_2$–$C_4$ hydroxyalkyl, benzyl or phenyl radical;

$R_4$ represents a hydrogen atom or a $C_1$–$C_6$ alkyl or $C_2$–$C_4$ hydroxyalkyl radical; with the proviso that $R_2$ represents a hydrogen atom when $R_1$ represents a substituted benzyl radical or forms a heterocycle with the nitrogen atom of $NR_3R_4$ in the 5-position;

at least one heterocyclic coupler selected from:

(i) indole derivatives of following formula (II), and the acid addition salts thereof:

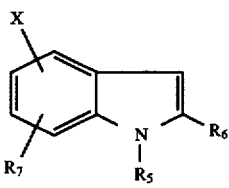

in which:

$R_5$ and $R_6$, which may be identical or different, represent a hydrogen atom or a $C_1$–$C_4$ alkyl radical;

$R_7$ represents a hydrogen atom or a $C_1$–$C_4$ alkyl or hydroxyl radical;

X represents a hydroxyl radical or a radical $NHR_8$ in which $R_8$ represents a hydrogen atom or a $C_1$–$C_4$ alkyl or $C_1$–$C_4$ hydroxyalkyl radical;

with the proviso that:
when $R_7$ denotes hydroxyl, it occupies the 6-position and X denotes hydroxyl and occupies the 5-position and $R_5$ and $R_6$ represent a hydrogen atom,
when X denotes hydroxyl and occupies the 4-position, at least one of the radicals $R_5$, $R_6$ and $R_7$ is other than a hydrogen atom,
when X is in the 5-position, at least one of the radical $R_5$, $R_6$ and $R_7$ is other than a hydrogen atom;

(ii) the benzimidazole derivatives of following formula (III), and the acid addition salts thereof:

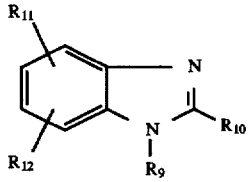

in which:

$R_9$ represents a hydrogen atom or a $C_1$–$C_4$ alkyl radical, $R_{10}$ represents a hydrogen atom or a $C_1$–$C_4$ alkyl or phenyl radical, $R_{11}$ represents a hydroxyl, amino or methoxy radical, or $C_1$–$C_4$ alkyl radical;

with the proviso that:
when $R_{11}$ denotes an amino radical, it occupies the 4-position,
when $R_{11}$ occupies the 4-position, $R_{12}$ occupies the 7-position,
when $R_{11}$ occupies the 5-position, $R_{12}$ occupies the 6-position;

(iii) the benzomorpholine derivatives of following formula (IV), and the acid addition salts thereof:

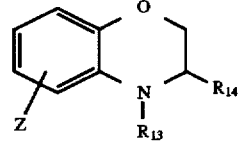

in which:

$R_{13}$ and $R_{14}$, which may be identical or different, represent a hydrogen atom or a $C_1$–$C_4$ alkyl radical, Z represents a hydroxyl or amino radical;

(iv) the pyridine derivatives of following formula (V), and the acid addition salts thereof:

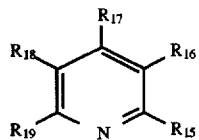

in which:

$R_{15}$ represents a hydrogen atom or a hydroxyl, amino or —OCH$_2$CH$_2$COCH$_2$CH$_2$OH radical.

$R_{16}$ and $R_{18}$, which may be identical or different, represent a hydrogen atom or a hydroxyl, amino or $C_1$-$C_4$ alkyl radical.

$R_{17}$ represents a hydrogen atom or a $C_1$-$C_4$ alkyl radical.

$R_{19}$ represents a hydrogen atom or a hydroxyl or amino radical, with the proviso that said compounds of formula (V) contain not more substituted or unsubstituted amino groups, not more than two hydroxyl groups, or not more than one amino group and one hydroxyl group per molecule, said amino, hydroxyl, or amino and hydroxyl groups necessarily being in a meta position relative to each other;

(v) indoline derivatives of following formula (VI), and the acid addition salts thereof:

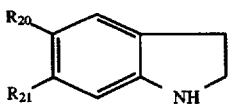

in which:

$R_{20}$ denotes a hydrogen atom or a hydroxyl radical, $R_{21}$, denotes a hydroxyl or amino radical;

(vi) the quinoline derivatives of following formula (VII), and the acid addition salts thereof:

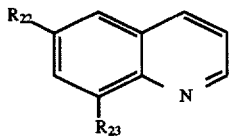

in which:

$R_{22}$ denotes a hydroxyl or $C_1$-$C_4$ alkoxy radical, $R_{23}$ denotes a hydrogen atom or amino radical;

(vii) the sesamol derivatives of following formula (VIII), and the acid addition salts thereof:

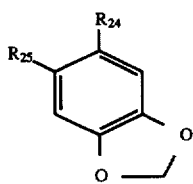

in which:

$R_{24}$ denotes a hydroxyl or amino radical, $R_{25}$ denotes a halogen atom or a $C_1$-$C_4$ alkoxy radical, with the proviso that:

when $R_{24}$ denotes an amino radical, $R_{25}$ denotes a $C_1$-$C_4$ alkoxy radical, when $R_{24}$ denotes a hydroxyl radical, $R_{25}$ denotes a halogen atom;

with the proviso that when said composition comprises a compound of formula (I) which is 4,5-diamino-1-methylpyrazole, it does not contain any indole derivative of formula (II) which is 5,6-dihydroxyindole, and wherein said at least one oxidation base and said at least one heterocyclic coupler are present in an amount effective to dye said keratin fibres.

2. A composition according to claim 1, wherein said keratin fibers are human keratin fibers.

3. A composition according to claim 2, wherein said human keratin fibers are hair.

4. A composition according to claim 1, wherein the acid addition salts are selected from the hydrochlorides, hydrobromides, sulphates and tartrates.

5. A composition according to claim 1, wherein the diaminopyrazole derivatives of formula (I) are selected from 4,5-diamino-1-(4'-methoxybenzyl)pyrazole, 4,5-diamino-1-(4'-methylbenzyl)pyrazole, 4,5-diamino-1-(4'-chlorobenzyl) pyrazole, 4,5-diamino-1-(3'-methoxybenzyl)pyrazole, 4-amino-1-(4'-methoxybenzyl)-5-methylaminopyrazole, 4-amino-5-(β-hydroxyethyl)amino-1-(4'-methoxybenzyl) pyrazole, 4-amino-5-(β-hydroxyethyl)amino-1-methylpyrazole, 4-amino-(3) 5-methylaminopyrazole, 3(5), 4-diaminopyrazole, 4,5-diamino-1-methylpyrazole, 4,5-diamino-1-benzylpyrazole, 3-amino-4,5,7,8-tetrahydropyrazolo[1,5-a]pyrimidine, 7-amino-2,3-dihydro-1H-imidazo[1,2-b]pyrazole and 3-amino-8-methyl-4,5,7,8-tetrahydropyrazolo[1,5-a]pyrimidine, and the acid addition salts thereof.

6. A composition according to claim 1, wherein the indole derivatives of formula (II) are selected from 6-hydroxyindole, 7-aminoindole, 6-aminoindole, 7-hydroxyindole, 7-ethyl-6-(β-hydroxyethyl)aminoindole, 4-aminoindole, 6-hydroxy-1-methylindole, 5,6-dihydroxyindole, 4-hydroxy-1-N-methylindole, 4-hydroxy-2-methylindole and 4-hydroxy-5-methylindole, and the acid addition salts thereof.

7. A composition according to claim 1, wherein the benzimidazole derivatives of formula (III) are selected from 4-hydroxybenzimidazole, 4-aminobenzimidazole, 4-hydroxy-7-methylbenzimidazole, 4-hydroxy-2-methylbenzimidazole, 1-butyl-4-hydroxybenzimidazole, 4-amino-2-methylbenzimidazole, 5,6-dihydroxybenzimidazole, 5-hydroxy-6-methoxybenzimidazole, 4,7-dihydroxybenzimidazole, 4,7-dihydroxy-1-methylbenzimidazole, 4,7-dimethoxybenzimidazole, 5,6-dihydroxy-1-methylbenzimidazole, 5,6-dihydroxy-2-methylbenzimidazole and 5,6-dimethoxybenzimidazole, and the acid addition salts thereof.

8. A composition according to claim 1, wherein the benzomorpholine derivatives of formula (IV) are selected from 6-hydroxy-benzomorpholine, N-methyl-6-hydroxy-benzomorpholine and 6-amino-benzomorpholine, and the acid addition salts thereof.

9. A composition according to claim 1, wherein the pyridine derivatives of formula (V) are selected from 2,6-dihydroxy-4-methylpyridine, 2,6-dihydroxy-3,4-dimethylpyridine, 2,6-diaminopyridine, 3-oxo-5-(3',5'-diamino-2'-pyridyloxy)pentanol and 3-(3',5'-diamino-2'-pyridyloxy)-2-hydroxypropanol, and the acid addition salts thereof.

10. A composition according to claim 1, wherein the indoline derivatives of formula (VI) are selected from 6-hydroxyindoline, 6-amino-indoline and 5,6-dihydroxyindoline, and the acid addition salts thereof.

11. A composition according to claim 1, wherein the quinoline derivatives of formula (VII) are selected from 6-hydroxyquinoline and 8-amino-6-methoxyquinoline, and the acid addition salts thereof.

12. A composition according to claim 1, wherein the sesamol derivatives of formula (VIII) are selected from 2-bromo-4,5-methylenedioxyphenol and 2-methoxy-4,5-methylenedioxyaniline, and the acid addition salts thereof.

13. A composition according to claim 1, wherein the at least one oxidation base selected from diaminopyrazole derivatives of formula (I) represents from 0.0005 to 12% by weight relative to the total weight of the dye composition.

14. A composition according to claim 1, wherein the at least one oxidation base selected from diaminopyrazole derivatives of formula (I) represents from 0.005 to 6% by weight relative to the total weight of the dye composition.

15. A composition according to claim 1, wherein the at least one heterocyclic coupler represents from 0.0001 to 10% by weight relative to the total weight of the dye composition.

16. A composition according to claim 15, wherein the at least one heterocyclic coupler represents from 0.005 to 5% by weight relative to the total weight of the dye composition.

17. A composition according to claim 1, wherein the medium suitable for dyeing consists of water or of a mixture of water and at least one organic solvent selected from $C_1$–$C_4$ lower alkanols, glycerol, glycols and glycolethers, aromatic alcohols, and mixtures thereof.

18. A composition according to claim 1, wherein said composition has a pH from 3 to 12.

19. A process for dyeing keratin fibers, said process comprising the steps of:

applying to said fibers an amount effective for developing color of a dye composition as defined in claim 1;

developing color at acidic, neutral or alkaline pH wherein said developing step comprises adding an effective amount of an oxidizing agent which is added to the dye composition only at the time said at least one dye composition is applied to said fibres or which is present in an oxidizing composition that is applied:

(i) separately from the dye composition at the same time that said dyeing composition is applied to said fibers or (ii) sequentially with the dye composition.

20. A process according to claim 19, wherein said keratin fibers are human keratin fibers.

21. A process according to claim 20, wherein said human keratin fibers are hair.

22. A process according to claim 19, wherein said oxidizing agent is selected from hydrogen peroxide, urea peroxide, alkali metal bromates and persalts.

23. A process according to claim 22, wherein said persalts are perborates or persulphates.

24. A multi-compartment device, or multi-compartment dyeing kit, comprising a first compartment containing a dye composition as defined in claim 1 and a second compartment containing an oxidizing composition.

* * * * *

UNITED STATES PATENT AND TRADEMARK OFFICE
CERTIFICATE OF CORRECTION

PATENT NO.: 5,785,717

DATED: July 28, 1998

INVENTOR(S): Mireille MAUBRU et al.

It is certified that an error appears in the above-identified patent and that said Letters Patent is hereby corrected as shown below:

IN THE CAIMS:

Claim 1, col. 10, line 43 should indent one space less and align with lines 39 and 41;

line 44, after "radical," (first occurrence) insert --$R_{12}$ represents a hydrogen atom or a hydroxyl, methoxy--; and col. 11, line 59 should indent one space less and align with line 58.

Signed and Sealed this

Twenty-ninth Day of September, 1998

Attest:

BRUCE LEHMAN

Attesting Officer

Commissioner of Patents and Trademarks